(12) United States Patent
Coleman et al.

(10) Patent No.: US 11,873,273 B2
(45) Date of Patent: Jan. 16, 2024

(54) ONLINE PRODUCTION OF ORGANIC PEROXIDE USING A CATALYST BED

(71) Applicant: SAFE FOODS CORPORATION, North Little Rock, AR (US)

(72) Inventors: Todd Coleman, Batesville, AR (US); Tim Yeaman, Russellville, AR (US); Slaton Fry, Conway, AR (US)

(73) Assignee: SAFE FOODS CORPORATION, North Little Rock, AR (US)

( * ) Notice: Subject to any disclaimer, the term of this patent is extended or adjusted under 35 U.S.C. 154(b) by 755 days.

(21) Appl. No.: 16/981,666

(22) PCT Filed: Mar. 28, 2019

(86) PCT No.: PCT/US2019/024516
§ 371 (c)(1),
(2) Date: Sep. 16, 2020

(87) PCT Pub. No.: WO2019/191387
PCT Pub. Date: Oct. 3, 2019

(65) Prior Publication Data
US 2021/0009515 A1 Jan. 14, 2021

Related U.S. Application Data

(60) Provisional application No. 62/649,988, filed on Mar. 29, 2018.

(51) Int. Cl.
| | | |
|---|---|---|
| C07C 407/00 | (2006.01) | |
| B01J 4/00 | (2006.01) | |
| B01J 8/00 | (2006.01) | |
| B01J 8/02 | (2006.01) | |

(52) U.S. Cl.
CPC ............ *C07C 407/00* (2013.01); *B01J 4/008* (2013.01); *B01J 8/001* (2013.01); *B01J 8/0278* (2013.01); *B01J 2204/005* (2013.01); *B01J 2208/00628* (2013.01); *B01J 2208/00823* (2013.01); *B01J 2208/00964* (2013.01)

(58) Field of Classification Search
CPC ........ B01J 2204/005; B01J 2208/00628; B01J 2208/00823; B01J 2208/00964; B01J 4/008; B01J 8/001; B01J 8/0278; C07C 407/00; C07C 409/26; G06F 3/1203; G06F 3/121; G06F 3/123; G06F 3/1234; G06F 3/1238; G06F 3/1293; G06F 3/1296; H04M 1/72409; H04N 1/0042; H04N 1/00344; H04N 1/00941; H04N 1/00954; E04H 12/24; G01R 31/50; H01B 17/14; H02G 1/02; H02G 7/20
See application file for complete search history.

(56) References Cited

U.S. PATENT DOCUMENTS

| | | |
|---|---|---|
| 5,122,538 A | 6/1992 | Lokkesmoe et al. |
| 9,845,290 B2 | 12/2017 | Balasubramanian et al. |
| 2008/0095677 A1* | 4/2008 | McSherry ............ C07C 407/00 422/117 |
| 2009/0314652 A1 | 12/2009 | Buschmann et al. |

FOREIGN PATENT DOCUMENTS

RU 2231045 C2 6/2004

OTHER PUBLICATIONS

Circulating definition (four pages. Downloaded from the internet Oct. 5, 2023) (Year: 2023).*
International Search Report and Written Opinion for International Application No. PCT/US2019/024516 dated Jul. 23, 2019, 15 pages.
Office Action for Russian Patent Application 2020135123 issued by the Federal Institute of Industrial Property (FIIP), dated Aug. 20, 2021, (7 pgs.).
English Translation of Office Action for Russian Patent Application 2020135123 issued by the Federal Institute of Industrial Property (FIIP), dated Aug. 20, 2021, (5 pgs.).
R. Pal et al. Amberlyst-15 in organic synthesis . Arkivoc, 2012 (i), 570-609, in particular, p. 572, section 2; Dowex DR-2030 and Dowex Monosphere DR-2030 Catalysis (https://www.tenntech.com/Data-sheets/Dowex- DR-2030-L.pdf), (4 pgs.).
Decision to Grant for Russian Patent Application 2020135123 issued by the Federal Institute of Industrial Property (FIIP), dated Feb. 1, 2022, (8 pgs.).
English Translation of Decision to Grant for Russian Patent Application 2020135123 issued by the Federal Institute of Industrial Property (FIIP), dated Feb. 1, 2022, (6 pgs.).
Office Action for Russian Patent Application 2020135123 issued by the Federal Institute of Industrial Property (FIIP), dated Feb. 19, 2021, (7 pgs.).
English Translation of Office Action for Russian Patent Application 2020135123 issued by the Federal Institute of Industrial Property (FIIP), dated Feb. 19, 2021, (7 pgs.).
Search Report for Russian Patent Application 2020135123 issued by the Federal Institute of Industrial Property (FIIP), dated Feb. 19, 2021, (2 pgs.).
English Translation of Search Report for Russian Patent Application 2020135123 issued by the Federal Institute of Industrial Property (FIIP), dated Feb. 19, 2021, (3 pgs.).
Considine, Glenn D., Van Nostrand's Scientific Encyclopedia || Peroxides and Peroxide Compounds (Organic), 2005, pp. 1-23.

(Continued)

*Primary Examiner* — Yevgeny Valenrod
*Assistant Examiner* — Blaine G Doletski
(74) *Attorney, Agent, or Firm* — Haynes and Boone, LLP; Randall C. Brown; Michael J. Tobin

(57) ABSTRACT

A method of producing an organic peroxide includes introducing an organic solution and a peroxide solution into a mixing tank to form a mixture. The method further includes circulating the mixture over a fixed catalyst bed to form the organic peroxide and measuring a concentration of the organic peroxide in the mixture. Further, the method includes removing at least a portion of the mixture when the concentration reaches a set value.

9 Claims, 1 Drawing Sheet

(56) References Cited

OTHER PUBLICATIONS

Moskvichev Yu.A. et al., Teoreticheskiye osnovy khimicheskoy tekhnologii: Uchebnoye posobiye. 2-ye izd., ispr.-SPb.: Izdatel'stvo "Lan", 2016 (In Russian )/ A.V. 2nd ed., Rev.-SPb.: Publishing House "Lan", 2016, (3 pgs.).

* cited by examiner

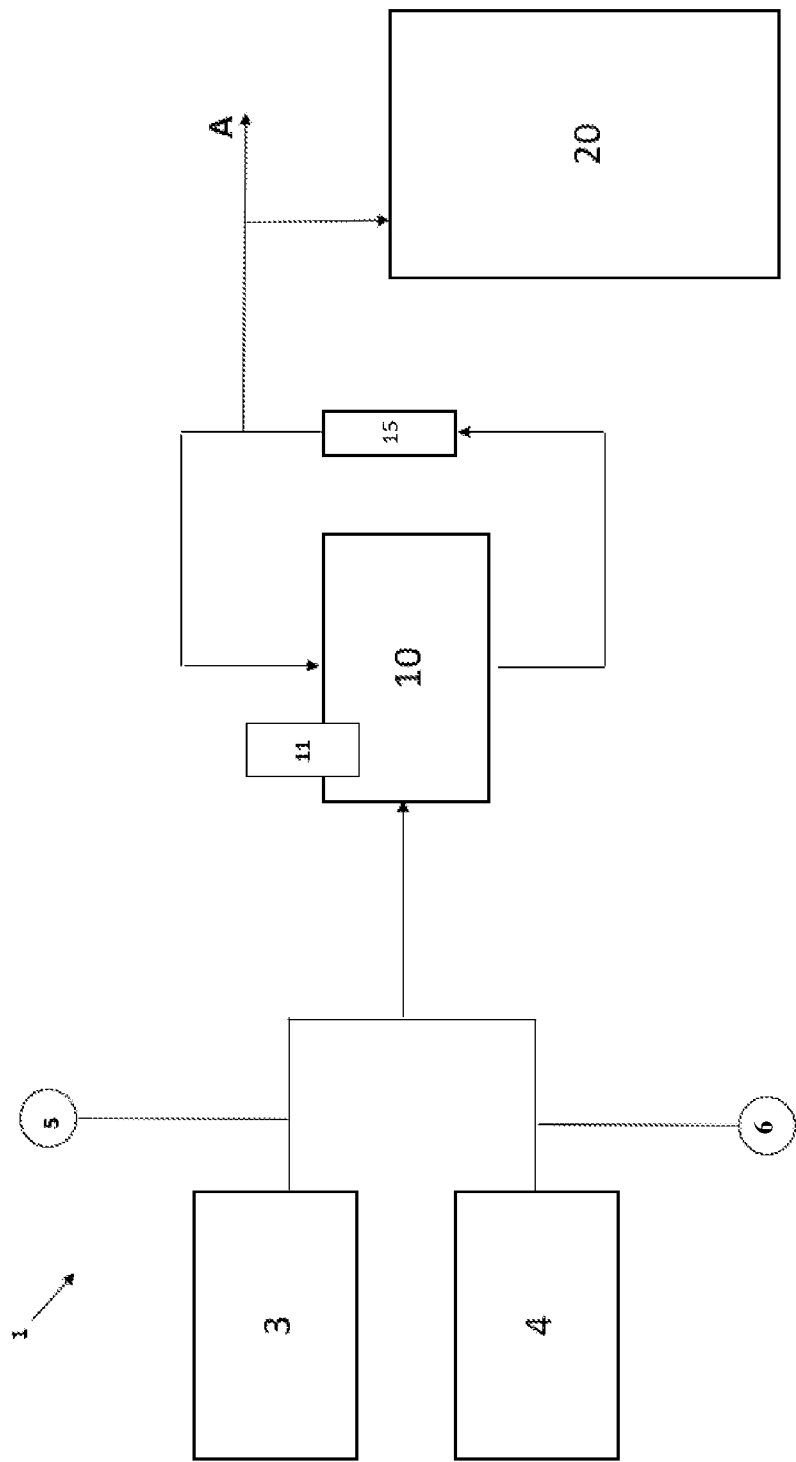

ONLINE PRODUCTION OF ORGANIC PEROXIDE USING A CATALYST BED

I. CROSS-REFERENCE TO RELATED APPLICATIONS

The present application is a U.S. National Stage patent application of International Patent Application No. PCT/US2019/024516 filed on Mar. 28, 2019, which claims the benefit of U.S. Provisional Patent Application No. 62/649,988 filed Mar. 29, 2018, titled "Online Production of Peroxyacetic Acid Using a Catalyst Bed," each of which is incorporated herein by reference in its entirety.

II. TECHNICAL FIELD

The present description relates to a method and system for producing organic peroxides.

III. BACKGROUND

Organic peroxides have a variety of uses. For instance, peroxyacetic acid (PAA) is a commonly used antimicrobial agent in the food industry and, in particular, in the poultry, pork, and beef processing industries. While PAA has been shown to be a very effective antimicrobial agent, its use has several drawbacks. Namely, PAA solutions are unstable under normal storage conditions and can lose potency over a relatively short time period. Additionally, PAA vapors represent a health risk to plant and federal inspection employees, and handling relatively concentrated solutions of PAA represents a potential exposure hazard to employees in processing plants. Moreover, transporting concentrated solutions of PAA on public transportation routes presents a potential exposure hazard to the general population.

IV. SUMMARY OF THE DISCLOSURE

Exemplary embodiments of the present disclosure relate to a method of producing an organic peroxide, in particular, PAA, online using a controlled mixing system that allows the simultaneous and precise control of the addition of a solution of hydrogen peroxide and a solution of an organic compound, such as acetic acid, to a mixing tank to provide the desired concentration of an organic peroxide (PAA) for direct application to poultry and beef carcasses. The present disclosure is also directed to a system for online production of an organic peroxide, such as PAA. The system eliminates the need to manufacture concentrated organic peroxide solutions and the need to transport these solutions to processing plants for subsequent dilution and application.

V. BRIEF DESCRIPTION OF THE DRAWINGS

Non-limiting and non-exhaustive embodiments of the present embodiments are described with reference to the following figure. It will be appreciated that elements in the figure are illustrated for simplicity and clarity and have not necessarily been drawn to scale. FIG. 1 is a schematic showing an embodiment of the present disclosure.

VI. DETAILED DESCRIPTION

While the present disclosure is described herein with reference to illustrative embodiments for particular applications, it should be understood that the disclosure is not limited thereto. Other embodiments are possible, and modifications can be made to the embodiments within the spirit and scope of the teachings herein and additional fields in which the embodiments would be of significant utility.

Referring to FIG. 1, the online production system 1 includes organic supply 3 and peroxide supply 4. The organic supply 3 provides an organic compound to be oxidized. Nonlimiting examples of suitable organic compounds include organic acids with 1 to 8 carbon atoms, such as acetic acid, citric acid, lactic acid, and dicarboxylic acids having 2 to 8 carbon atoms. The peroxide supply 4 provides a peroxide, such as hydrogen peroxide, which is capable of oxidizing the organic compound. Each of supplies 3 and 4 are in fluid communication with mix tank 10.

Organic supply 3 may be in fluid communication with a water supply 5. Flow rates from organic supply 3 and water supply 5, respectively, may be independently adjusted accordingly to provide a desired concentration of the organic compound within an organic solution to be supplied to mix tank 10. For instance, the organic solution may include 10-50 wt % of the organic compound, e.g., 15-40 wt %, 15-35 wt %, 15-30 wt %, 20-35 wt %, 20-30 wt %, 10 wt %, 15 wt %, 20 wt %, 25 wt %, 30 wt %, 35 wt %, or 40 wt %. In some embodiments, the organic solution is diluted to the desired concentration before entering the system 1. In some embodiments, water may be supplied directly to the mix tank 10 rather than being mixed with the organic compound first.

Peroxide supply 4 may be in fluid communication with a water supply 6. Flow rates from peroxide supply 4 and water supply 6, respectively, may be independently adjusted accordingly to provide a desired concentration of the peroxide within a peroxide solution to be supplied to mix tank 10. For instance, the peroxide solution may include 10-50 wt % of the peroxide, e.g., 10-30 wt %, 10-20 wt %, 15-40 wt %, 15-35 wt %, 15-30 wt %, 20-35 wt %, 20-30 wt %, 5 wt %, 10 wt %, 15 wt %, 20 wt %, 25 wt %, 30 wt %, 35 wt %, or 40 wt %. In some embodiments, the peroxide solution is diluted to the desired concentration before entering the system 1. In some embodiments, water may be supplied directly to the mix tank 10 rather than being mixed with the peroxide first.

The order of adding the organic solution and the peroxide solution into the mix tank 10 is not particularly limited. In some embodiments, the organic solution may be added first, the peroxide solution may be added first, the organic solution and the peroxide solution may be added simultaneously, or the organic solution and the peroxide solution may be alternatingly added to the mix tank 10. In any embodiment, the organic solution and the peroxide solution may be added to the mix tank 10 through a single line as shown in FIG. 1 or through separate lines (not shown).

In some embodiments, a first solution (either the organic solution or the peroxide solution) is provided to the mix tank 10 until the mix tank 10 reaches a first specified capacity, such as 10 vol %, 20 vol %, 30 vol %, 40 vol %, 50 vol %, or 60 vol %. Thereafter, the other solution is added until the mix tank 10 reaches a second specified capacity. The second specified capacity may be, e.g., 10 vol %, 20 vol %, 30 vol %, 40 vol %, 50 vol %, or 60 vol % greater than the first specified capacity. In some embodiments, the organic solution and the peroxide solution are simultaneously added to the mixing tank until the capacity reaches, e.g., 60 vol %, 70 vol % 80 vol %, 90 vol %, or 100 vol %.

Once the organic solution and peroxide solution have been added to the mix tank 10, the mixture may be circulated through a catalyst bed 15. The catalyst bed 15 includes a catalyst that facilitates the reaction between the organic compound and the peroxide to thereby form an organic peroxide. The catalyst bed 15 may include an acid resin. The acid resin is not particularly limited and may include, e.g., acid resins under the following trade names: Amberlite® IR120 Plus, Amberlyst® 15, Amberlyst® 36, Dowex® 50WX2, Dowex® 50WX4, Dowex® 50WX8, Dowex® HCR-S, Dowex® 650C, Dowex® Marathon C, Dowex® DR-2030 (each available from The Dow Chemical Company), Nafion® NR40, or Nafion® NR50 (each available from DuPont). During or before circulation, the mixture may be heated to, e.g., 30° C., 35° C., 40° C., 45° C., or 50° C.

The system 1 includes a sensor 11 to measure a conversion rate of the organic compound and the peroxide to an organic peroxide, e.g., by continuously or intermittently measuring a concentration of organic peroxide in the solution. For instance, in embodiments wherein the organic peroxide is PAA, the sensor 11 may be a PAA probe that measures the concentration of PAA in the solution. The location of the sensor 11 is not particularly limited. For example, the sensor may be inside or connected to the mix tank 10, as shown in FIG. 1. In some embodiments, more than one sensor 11 is provided, and in such embodiments, the sensors 11 may be the same or different from one another. In some embodiments, the circulation of the mixture from the mix tank 10 to the catalyst bed 15 may be stopped after a specified period of time or once the sensor 11 detects a target concentration of the organic peroxide in the organic peroxide solution. For instance, the target concentration may be between 10 ppm and 10,000 ppm, inclusive, based on the total mass of the mixture. For instance, based on the total mass of the mixture, a target concentration may be 10 ppm, 20 ppm, 30 ppm, 40 ppm, 50 ppm, 75 ppm, 100 ppm, 125 ppm, 150 ppm, 200 ppm, 250 ppm, 300 ppm, 350 ppm, 400 ppm, 450 ppm, 500 ppm, 550, ppm, 600 ppm, 650 ppm, 700 ppm, 750 ppm, 800 ppm, 900 ppm, 1,000 ppm, 1,100 ppm, 1,200 ppm, 1,300 ppm, 1,400 ppm, 1,500 ppm, 1,600 ppm, 1,700 ppm, 1,800 ppm, 1,900 ppm, or 2,000 ppm.

Once the organic peroxide solution or a portion thereof within the system 1 has reached the target concentration, the organic peroxide solution may be removed from the circulation. The organic peroxide solution may be diverted as needed depending on the requirements of the operation. For instance, as shown by arrow A in FIG. 1, all or a portion of the organic peroxide solution may be directed to various application points. In embodiments where the organic peroxide solution has antimicrobial properties, such as PAA, various applications of the organic peroxide solution are described below. In some embodiments, all or a portion of the organic peroxide solution may be temporarily stored in an in-process tank 20. In any embodiment, the organic solution and peroxide solution may be continuously added to the mix tank 10, e.g., at a rate equal to the rate of the organic peroxide solution being removed. In some embodiments, the present disclosure relates to a method for processing a food product, the method comprising sanitizing a food product with regard to at least one microorganism. In some embodiments, sanitizing a food product with regard to at least one microorganism may comprise contacting the food product with the organic peroxide solution described herein. In various embodiments, the microorganisms may comprise Gram-positive bacteria, Gram-negative bacteria, fungi, protozoa or a combination thereof. The Gram-negative bacteria may comprise *Salmonella, Campylobacter, Arcobacter, Aeromonas*, non-toxin-producing *Escherichia*, pathogenic toxin-producing *Escherichia* or a combination thereof. The Gram-positive bacteria may comprise *Staphylococcus,* *Bacillus, Listeria*, or a combination thereof. The fungi may comprise *Aspergillus flavus, Penicillium chrysogenum*, or a combination thereof. The protozoa may comprise *Entomoeba histolytica*.

In some embodiments, the present disclosure relates to a method of sanitizing a workpiece with regard to at least one microorganism, the method comprising contacting the workpiece with the organic peroxide solution described herein. The microorganism may, for example, be as described above. The workpiece may, for example, include food packaging, items and surfaces related to food or food processing, or items and surfaces unrelated to food or food processing.

In the methods of sanitizing described herein, the mode of applying organic peroxide solution is not particularly limited. Methods of application may include, but are not limited to, spraying, misting, fogging, immersing, pouring, dripping, and combinations thereof. Some methods of sanitizing relate to sanitizing food products or equipment during harvest and processing of the food product. Throughout the harvest process, there are many opportunities for antimicrobial interventions, and determining what works most effectively at each step may differ from processor to processor. As such, the timing of applying the organic peroxide solution to the target article is not particularly limited. In some embodiments, the organic peroxide solution may be applied to a food product prior to an evisceration process so as to adhere to the food product throughout the evisceration process, as well as when coming into contact with equipment, viscera, and humans.

In embodiments wherein the target article is poultry, the organic peroxide solution may be applied in the processing facility in several different locations to include, but not be limited to, the following: during the pick operation to post-picking prior to evisceration, onto evisceration equipment during operation, online reprocessing (OLR) location, offline reprocessing (OFLR) location, pre-chill location, chillers, post-chill, on carcass frames post debone, and on various poultry parts in numerous locations in the plant. In embodiments wherein the target article is beef or pork, the organic peroxide solution may be applied in the processing facility in several different locations to include, but not be limited to, the following: hide on carcass application, equipment used during the harvest process, knife dip station, beef carcass application, sub-primal application, lean trimming application, and ground beef applications. In embodiments wherein the target article is fruit or vegetables, the organic peroxide solution may be applied in the processing facility in several different locations to include, but not be limited to, the following: all loading/unloading, all treatment pre-and post-flume, and prior and post to all cut up and smash treatment.

In embodiments where the organic peroxide solution is PAA, the stability of PAA may be affected by the ratio of components (e.g., acetic acid, hydrogen peroxide, and water) used to generate the PAA. Further, in any embodiment, the stability of the organic peroxide solution may be impacted by environmental considerations such as ambient temperature, direct sunlight, and storage location.

Generation of PAA online with immediate use would eliminate the need for stabilizing compounds such as etidronic acid. Etidronic acid is a phosphorous containing compound that will eventually be deposited in waste water treatment systems. Phosphate compounds can lead to eutrophication in the environment.

Equivalents and alternatives along with obvious changes and modifications are intended to be included within the scope of the present disclosure. Accordingly, the foregoing disclosure is intended to be illustrative, but not limiting, of the scope of the disclosure as illustrated by the appended claims.

EXAMPLES

Example 1

One ml of concentrated PAA (containing 15-17% of PAA by weight on the day of formulation) was mixed in one gallon of water. The concentration of the diluted solution was measured using a standard PAA titration kit. Measurements were taken at one-week intervals for a total of 16 weeks. The results are summarized in Table 1 below.

TABLE 1

| Week after initial formulation | PAA Concentration |
| --- | --- |
| Week 1 | 70-75 ppm |
| Week 2 | 60 ppm |
| Week 3 | 60-65 ppm |
| Week 4 | 50 ppm |
| Week 5 | 55 ppm |
| Week 6 | 40-45 ppm |
| Week 7 | 50-55 ppm |
| Week 8 | 50 ppm |
| Week 9 | 40-45 ppm |
| Week 10 | 40-45 ppm |
| Week 11 | 40-45 ppm |
| Week 12 | 40 ppm |
| Week 13 | 45 ppm |
| Week 14 | 55-60 ppm |
| Week 15 | 40-45 ppm |
| Week 16 | 35-40 ppm |

As shown above, the solution had a maximum PAA concentration after 1 week, and the PAA concentration decreased as the solution aged. These results confirm the volatile nature of PAA and the need for online production to ensure sufficient PAA concentration for antimicrobial applications.

The above specific example embodiments are not intended to limit the scope of the claims. The example embodiments may be modified by including, excluding, or combining one or more features or functions described in the disclosure. The description of the present disclosure has been presented for purposes of illustration and description but is not intended to be exhaustive or limited to the embodiments in the form disclosed. Many modifications and variations will be apparent to those of ordinary skill in the art without departing from the scope and spirit of the disclosure. The illustrative embodiments described herein are provided to explain the principles of the disclosure and the practical application thereof, and to enable others of ordinary skill in the art to understand that the disclosed embodiments may be modified as desired for a particular implementation or use. The scope of the claims is intended to broadly cover the disclosed embodiments and any such modification.

What is claimed is:

1. A method of producing an organic peroxide comprising:
    introducing an organic solution and a peroxide solution into a mixing tank to form a mixture;
    circulating the mixture over a fixed catalyst bed to form the organic peroxide;
    measuring a concentration of the organic peroxide in the mixture; and
    removing at least a portion of the mixture when the concentration reaches a set value.

2. The method according to claim 1, wherein the peroxide solution comprises hydrogen peroxide and water.

3. The method according to claim 2, wherein the peroxide solution comprises 10 to 50 wt % of hydrogen peroxide based on a total weight of the peroxide solution.

4. The method according to claim 1, wherein the organic solution comprises water and an organic acid having 1 to 8 carbon atoms.

5. The method according to claim 4, wherein the organic solution comprises 10 to 50 wt % of the organic acid based on a total weight of the organic solution.

6. The method according to claim 4, wherein the organic acid is acetic acid.

7. The method according to claim 5, wherein the organic acid is acetic acid.

8. The method according to claim 1, wherein the fixed catalyst bed comprises an acid resin.

9. The method according to claim 1, wherein the set value is between 50 and 2000 ppm of the organic peroxide.

* * * * *